United States Patent
Heesch

(10) Patent No.: US 6,544,502 B2
(45) Date of Patent: Apr. 8, 2003

(54) SKIN TREATMENT WITH A WATER SOLUBLE ANTIBIOTIC DISSOLVED IN AN ELECTROLYZED WATER

(75) Inventor: Gary V. Heesch, Salt Lake City, UT (US)

(73) Assignee: Wasatch Pharmaceutical Inc., Salt Lake City, UT (US)

( * ) Notice: Subject to any disclaimer, the term of this patent is extended or adjusted under 35 U.S.C. 154(b) by 154 days.

(21) Appl. No.: 09/858,261

(22) Filed: May 15, 2001

(65) Prior Publication Data

US 2002/0165220 A1 Nov. 7, 2002

Related U.S. Application Data

(63) Continuation of application No. 08/585,457, filed on Jan. 16, 1996, now abandoned, which is a continuation-in-part of application No. 08/153,611, filed on Nov. 17, 1993, now abandoned, which is a continuation-in-part of application No. 07/944,051, filed on Sep. 11, 1992, now abandoned.

(51) Int. Cl.$^7$ .......................... A61K 7/09; A61K 31/74
(52) U.S. Cl. .............................. 424/70.21; 424/78.05; 424/78.07; 424/176.1; 514/859; 514/861; 514/863; 514/864; 514/887

(58) Field of Search ............................ 424/70.21, 78.05, 424/78.07, 176.1; 514/859, 863, 864, 861, 887

(56) References Cited

FOREIGN PATENT DOCUMENTS

JP          339152       * 12/1993

OTHER PUBLICATIONS

Baraldi, et al. J. of Medicinal Chemistry Aug. 2, 2001 vol. 44 No. 16 pp 2536–2543.*

* cited by examiner

*Primary Examiner*—Paul J. Killos
(74) *Attorney, Agent, or Firm*—Lynn G. Foster

(57) ABSTRACT

A method for treating a skin condition by intimately combining a water soluble antibiotic with the keratin layer of the outermost layer of the cleansed epidermis. The antibiotic is dissolved in the alkaline fraction of an electrolyzed water. The solution is characterized by the absence of hydrolysis products, turbidity, and loss of potency of the antibiotic. The aqueous solution is applied to the treatment area where the water is absorbed by the keratin and the antibiotic is carried into intimate contact with the keratin after which the water is evaporated leaving the antibiotic dispersed across the treatment area.

20 Claims, 1 Drawing Sheet

SKIN TREATMENT WITH A WATER SOLUBLE ANTIBIOTIC DISSOLVED IN AN ELECTROLYZED WATER

RELATED APPLICATIONS

This application is a continuation application of my copending application Ser. No. 08/585,457, filed Jan. 16, 1996 now abandoned, which is a continuation-in-part of Ser. No. 08/153,611 filed Nov. 17, 1993 for SKIN TREATMENT WITH AN AQUEOUS SOLUTION OF A WATER SOLUBLE ANTIBIOTIC now abandoned, which was a continuation-in-part application of my application Ser. No. 07/944,051 filed Sep. 11, 1992 for SKIN TREATMENT (now abandoned).

BACKGROUND

1. Field of the Invention

This invention relates to the treatment of certain skin conditions, and, more particularly, to the novel discovery that the topical application of a freshly prepared aqueous solution of a water soluble antibiotic in an electrolyzed water and in a carefully prescribed fashion contributes significantly to the healing process of these certain skin conditions, several of which historically have not been considered amendable to any treatment protocol involving antibiotics. The treatment methodology has also proven efficacious in preventing the flare up of acne in susceptible patients.

2. The Prior Art

The skin is the largest organ of the human body. It is composed of tissue that grows, differentiates, and renews itself constantly. Since the skin is a generally impermeable membrane, it acts as a barrier between the internal organs and the external environment, and it is, therefore, uniquely subjected to noxious external agents and is also a sensitive reflection of internal disease.

Various diseases affect the skin. These include, for example, acne, eczema, and psoriasis, to name a few. Numerous theories have been postulated for the cause or causes of, say, acne with professionals in the medical community disputing almost everything about it except its existence. The disputes about acne include its causation, histopathology, pathophysiology, treatment, and even the role of diet in acne flare-ups.

Numerous patents have issued for various acne treatments and generally involve the application of selected substances or combinations of substances to the skin. All known acne treatments using topically applied products have met with only limited success in the treatment of acne conditions. None of these topically applied products are known for the treatment of cystic acne conditions. Further, none are considered as a preventative treatment for acne.

Many topically applied products include an antibiotic in a lotion base along with numerous other ingredients including preservatives and the like. It is my contention that the lotions, preservatives, etc., interfere with the antibacterial activity of the antibiotic both directly by masking its presence with the topical creme as well as by chemically interacting with the antibiotic molecule. Oils are especially detrimental for a water-based antibiotic because it is through the aqueous medium that the antibiotic is optimally effective. In other words, the empirical evidence demonstrates that the delivery vehicle, ie., the lotion base with all its various ingredients, compromises the integrity or potency of the topical antibiotic.

Further, historically, the treatment of, say, acne is significantly different from the treatment of other skin diseases such as eczema, psoriasis, dermatitis, and the like. Each skin condition is subjected to a different treatment protocol, none of which involve the topical application of an aqueous solution of an antibiotic.

Young (U.S. Pat. No. 3,883,661) teaches the treatment of acne by topically applying a member of a certain class of fatty acid amides to the affected skin area. Oleic acid diethanolamide is illustrated as a representative of the useful class.

Kligman (U.S. Pat. No. 3,729,568) teaches the topical application of vitamin A acid to the affected area as a treatment for acne vulgaris. The vitamin A acid is preferably applied in a liquid solvent. A composition found to be particularly effective is vitamin A acid dispersed in small amounts in a water-miscible liquid carrier made up of hydrophilic liquids having a high solvating action.

Nelson (U.S. Pat. No. 4,323,558) teaches the use of pharmaceutical compositions containing triethylenetetramine (trien) for the treatment of skin disorders such as acne, seborrhea, and dermatitis. The trien appears to have a certain degree of anti-inflammatory activity.

Other references teach the use of antibiotics for the treatment of acne conditions. These antibiotics are either taken orally or mixed in some form of emollient base and applied topically to the skin. For those applied topically, a certain proportion of the antibiotic has been known to become absorbed through the skin due to the ability of the lipid-based emollient to penetrate the skin to a certain degree. Further, it is postulated that certain emollient-like carrier creams may exacerbate an acne condition by contributing to the blockage of the normal sebum flow as will be discussed more fully hereinafter.

In view of the foregoing, it would be an advancement in the art to provide a skin treatment that is beneficial for a variety of skin conditions including such conditions as acne, eczema, and psoriasis, to name a few. It would be a particularly significant advancement in the art to dissolve a water soluble antibiotic in an electrolyzed water, the electrolyzed water having a higher affinity for the keratin layer of the skin thereby more intimately carrying the antibiotic into intimate dispersion across the surface of the skin. It would be an even further advancement in the art to provide a skin treatment that is particularly characterized by the absence of harsh chemicals, noxious substances, ointments, and the like. It would also be an advancement in the art to provide a skin treatment protocol whereby antibiotic is delivered downwardly into the upper end of the follicular canal to thereby directly attack the bacterial component of an acne flare up. An even further advancement in the art would be to provide a skin treatment that has minimal side effects so that it can be used even by pregnant women. It is a significant advancement when the therapy in question is preventative in nature, and in a major percentage of patients treated (hundreds) a cure has been demonstrated and documented. Such a novel invention is disclosed and claimed herein.

BRIEF SUMMARY AND OBJECTS OF THE INVENTION

This invention relates to a novel skin treatment methodology for treating various skin conditions such as acne, eczema, psoriasis, and the like, with a freshly prepared solution of a water soluble antibiotic. Importantly, the water soluble antibiotic is dissolved in electrolyzed water, more specifically, the alkaline fraction of the electrolyzed water. The ability of the keratin layer of the epidermis to absorb a vast amount of water coupled with the fact that the water is primarily constituted of the alkaline fraction of the electrolyzed water causes the antibiotic to become intimately dispersed throughout the keratin layer on the surface of the skin. The underlying epidermis prevents the water and any significant quantity of antibiotic from being absorbed into the epidermis and underlying dermis. The treatment includes cleansing the hands followed by cleansing the affected area of the skin using a mild, water-based cleansing agent. For acne conditions, the cleansing step includes the application of an alcohol to the treatment area to help rid the treatment area of both excess oils and any residual bacteria, whether aerobic or anaerobic bacteria, that may be present. A freshly prepared, aqueous solution of a water soluble, broad spectrum antibiotic such as a soluble salt of doxycycline is then applied to the area and allowed to air dry. The water in the solution is obtained as the alkaline fraction of an electrolyzed water so that it is readily absorbed by the keratin layer thereby dispersing the antibiotic intimately over the surface of the skin. Importantly, particularly in the treatment of acne, the high affinity of the keratin layer for this type of water causes the antibiotic to be directed downwardly into the follicular canal through the keratin lining of the follicular canal where it more effectively suppresses the bacteria found there. An important following step in the treatment protocol is maintaining the treated area, to the extent practicable, free from contact with objects that could possibly recontaminate the treated area. The treated area can be covered with a suitable skin creme to help seal the antibiotic to the skin. The treatment process is repeated at least twice a day.

It is, therefore, a primary object of this invention to provide improvements in skin treatments for skin diseases such as acne, eczema, psoriasis, and the like.

Another object of this invention is to intimately disperse an antibiotic throughout the keratin layer of the epidermis where it will readily destroy bacteria on the skin.

Another object of this invention is to provide the alkaline fraction of an electrolyzed water as the solvent for the water soluble antibiotic.

Another object of this invention is to provide a skin treatment that is characterized by the absence of harsh chemicals.

Another object of this invention is to provide a water soluble antibiotic that can be applied as an aqueous solution where the water in the aqueous solution is readily absorbed in the keratin and thereby intimately disperse the antibiotic throughout the surface of the skin of the treated area.

Another object of this invention is to preclude the absorption of the antibiotic into the underlying skin by applying the antibiotic to the skin as an aqueous solution of a water soluble antibiotic.

Another object of this invention is to prepare a fresh solution of antibiotic and water to assure maximum potency of the antibiotic.

Another object of this invention is to provide a water soluble antibiotic that can be applied to the skin following the application of an alcohol for the treatment of acne.

Another object of this invention is to provide a preventative treatment methodology for use in preventing the onset of acne.

Another object of this invention is to provide a skin treatment that is safe for use even by pregnant women.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
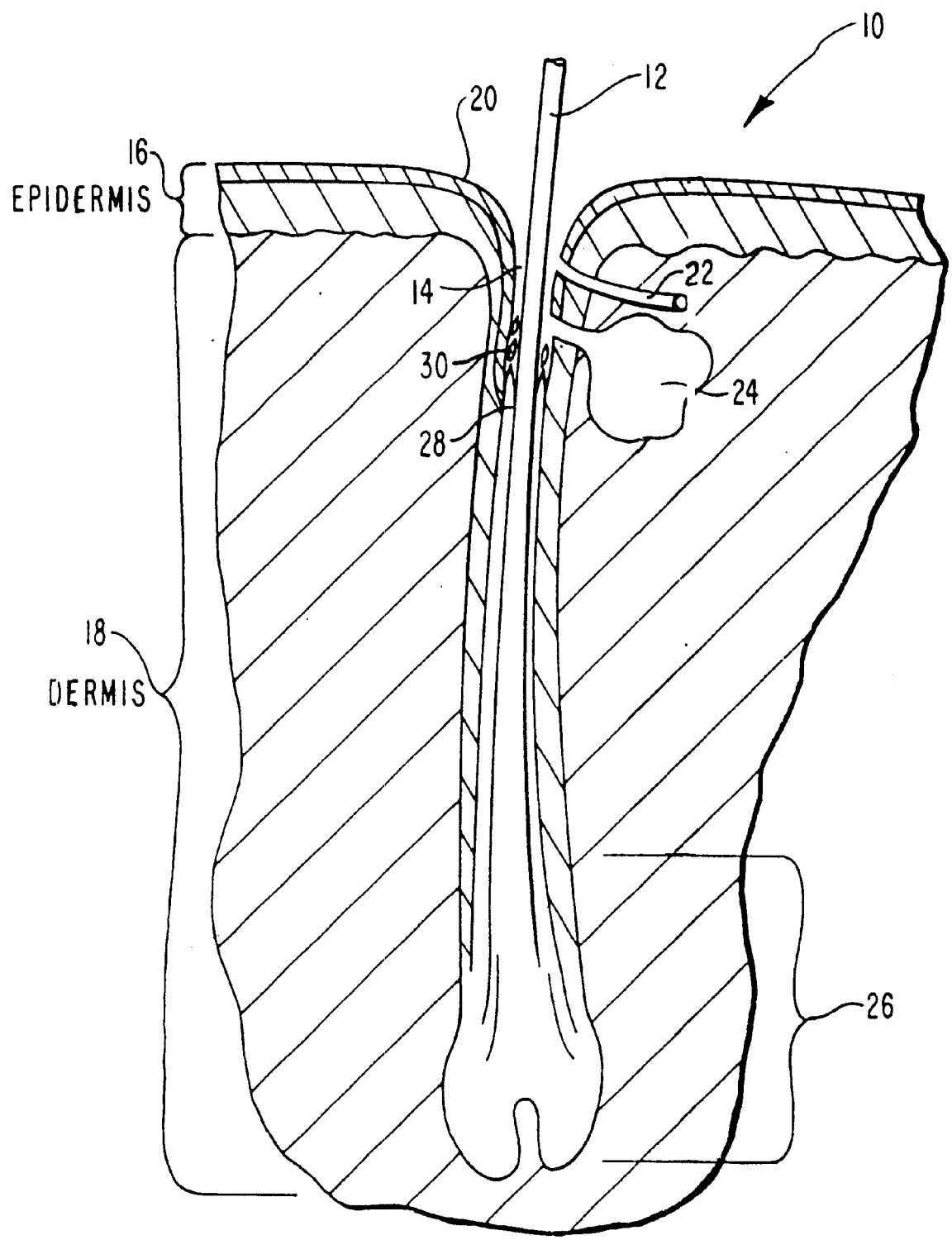
FIG. 1 is an enlarged, schematic, cross-sectional view of a follicle.

The invention is best understood by reference to the drawing wherein like parts are designated by like numerals throughout in conjunction with the following description.

General Discussion

Electrolyzed Water

Electrolyzed water or, more particularly, the alkaline fraction of the electrolyzed water has been found to significantly reduce the treatment times over that of using plain water. At the present time I am unable to adequately explain this phenomena, but in our clinics we have observed significantly reduced treatment times for our patients when we use the alkaline fraction of the electrolyzed water. The alkaline fraction of an electrolyzed water is obtained according to the teachings of U.S. Pat. No. 5,051,161 and is commercially available as a water filter having an electrolyzing filter sold commercially by Mizutek International, Inc., having a business address at 3760 Highland Drive, Fourth Floor, Salt Lake City, Utah 84106.

Even though we are unable to explain this surprising and unexpected result from using the alkaline fraction, it is postulated that possibly the alkaline fraction retards the degradation of the antibiotic so that it retains its potency at a higher level for a longer period of time. Also, it is possible that the alkaline fraction may exhibit a certain detergent-like effect to enhance the dispersion of the antibiotic into the keratin layer and especially down into the follicular canal.

The Structure of the Skin

The skin is divided into three rather distinct layers. From the inside out, they are the subcutaneous tissue, the dermis, and the epidermis. The subcutaneous tissue serves as a receptacle for the formation and storage of fat, is a locus of highly dynamic lipid metabolism, and supports the blood vessels and the nerves that pass from the tissues beneath to the dermis above. The deeper hair follicles and the sweat glands originate in this layer.

The dermis is made up of connective tissue, cellular elements, and ground substance. It has a rich blood and nerve supply. The sebaceous glands and the shorter hair follicles originate in the dermis. The connective tissue consists of collagen fibers, elastic fibers, and reticular fibers. All of these, but most importantly the collagen fibers, contribute to the support and elasticity of the skin. The cellular elements of the dermis consist of three groups of mesodermal cells: a reticulohistiocytic group, a myeloid group and a lymphoid group. Under pathologic conditions, the potentiality of these cells can change.

The reticulohistiocytic group consists of fibroblasts, histiocytes, and mast cells. The immature cells of the reticulohistiocytic group are known as reticulum cells. Fibroblasts form collagen fibers and may be the progenitors of all other connective tissue cells. The histiocytes normally are present in small numbers around blood vessels, but in pathologic conditions they can migrate in the dermis as tissue monocytes. When they phagocytize bacteria and particulate matter, they are known as macrophages. Further, under special pathologic conditions, histiocytes can also change into epithelioid cells, which in turn can develop into so-called giant cells.

The last group of histiocytic cells, mast cells, have intracytoplasmic basophilic metachromatic granules containing heparin and histamine. Normal skin contains relatively few mast cells, but their number is increased in many different skin conditions, particularly the itching dermatoses, such as atopic eczema, contact dermatitis, and lichen planus. In urticaria pigmentosa the mast cells occur in tumor-like masses.

Plasma cells, rarely seen in normal skin sections, occur in small numbers in most chronic inflammatory diseases of the skin and in larger numbers in granulomas. The origin of plasma cells is unknown, but they are believed to arise from reticulum cells.

In the myeloid group of cells, the polymorphonuclear leukocyte and the eosinophilic leukocyte occur quite commonly with various dermatoses, especially those with an allergic etiology. In the lymphoid group, the lymphocyte is commonly found in inflammatory lesions of the skin. The myeloid and the lymphoid groups of cells are also found in their specific neoplasms of the skin.

The ground substance of the dermis is a gel-like, amorphous matrix not easily seen histologically, but it is of tremendous physiologic importance since it contains proteins, mucopolysaccharides, soluble bodies, metabolites, and many other substances.

The epidermis is the most superficial of the three layers of the skin and averages in thickness less than about one millimeter. There are two distinct types of cells in the epidermis, the keratinocytes and the dendritic cells, or clear cells. The keratinocytes, or keratin-forming cells, are found in the basal layer and give rise to all the other cells of the stratified epidermis. The dendritic cells are of three types; melanocytes (melanin-forming cells), langerhans cells, and indeterminate dendritic cells.

The epidermis is divided into five layers that include the following (from inside out): basal layer, prickle layer, granular layer, lucid layer, and horny layer. The basal layer of cells lies next to the corium and contains both keratin-forming and melanin-forming cells. The keratin-forming cells can be thought of as stem cells, which are capable of progressive differentiation into the cell forms higher up in the epidermis. It normally requires three or four weeks for the epidermis to replicate itself by the process of division and differentiation. This cell turnover is greatly accelerated in such diseases as psoriasis and ichthyosiform erythroderma.

The prickle layer, or stratum malpighii, is made up of several layers of epidermal cells, chiefly of the polyhedral shape, and gets its name from the existence of a network of cytoplasmic threads called prickles, or intercellular bridges, that extend between cells. These prickles are most readily visible in this layer but, to a lesser extent, are present between all cells in the epidermis.

The granular layer is the third layer and consists of cells that are flatter and contain protein granules called keratohyalin granules.

The lucid layer is the fourth layer and appears as a translucent line of flat cells. This layer is present only on the palms and soles. The granular and the lucid layers make up the transitional layer of the epidermis and act as a barrier to the inward transfer of noxious substances and the outward loss of water.

The outermost layer of the epidermis is the horny layer and is made up of stratified layers of dead keratinized cells that are constantly shedding. The chemical protein in these cells, keratin, is capable of absorbing a vast amount of water.

The Immune Response

Although the skin has long been thought of as an effective, albeit passive, barrier between the internal organs of humans and their environment, it is now clear that it is not an inert shield but instead a major participant in the complex immunologic reactions that protect humans against foreign antigens. The skin is the most exposed of all epithelial surfaces, separated from irritants, toxins, and microorganisms by a thin barrier of dried epithelial cells. Because it is so accessible, minor degrees of inflammation are readily observed. Whether the triggering agent is a bacterial infection such as impetigo, bacterial and lipid products as in acne, or a contact allergen as in poison ivy, the common denominator is the tissue change upon cellular breakdown induced by the humoral and/or cellular mediators of the immune response.

The main purpose of the immune response is its active role in recognizing foreign substances (antigens) and implementing their removal from the host. This role response is complex because antigens differ: some are large, some are small; some are polysaccharides, some are proteins; some are soluble, some are tightly bound to cells; some are presented in the circulation, some in tissue, some on mucosal surfaces, and some to the stratum corneum. The immune response can be divided in a number of different ways. First, there is both an afferent and efferent limb. The afferent limb refers to the events between initial exposure to an antigen and developing hypersensitivity to it, while the efferent limb refers to the events producing inflammation as the specific immune response is amplified in response to the antigen.

There are both nonspecific and specific responses. The former occur in many situations without evoking immunologic memory, such as when the body reacts to a splinter. The latter require earlier exposure to an antigen and then an antigen-specific response involving memory cells. Many factors are responsible for nonspecific immune response. The main one is phagocytosis, in which polymorphonuclear white blood cells and monocytes and macrophages from the circulation and a variety of tissues engulf foreign objects. This process can be enhanced by cells and soluble products of the specific immune response. The complement cascade can also be nonspecifically initiated to produce inflammation. Finally, some specialized lymphocytes (natural killer, or NK, cells) and eosinophils can attack foreign cells, such as tumor cells, or parasites without specific recognition or sensitization.

The Structure of the Follicle

Referring now to FIG. 1, the fully developed follicle or pilosebaceous unit is shown generally at 10 in this enlarged, cross-sectional schematic view and includes a keratinized hair shaft 12 extending outwardly from a follicular canal 14. The follicular canal 14 extends through the epidermis 16 and into the dermis 18 with the horny layer or keratin layer 20 of epidermis 16 forming a portion of the lining of follicular canal 14. The duct of the apocrine gland (not shown) is shown as apocrine duct 22 and opens into follicular canal 14. A sebaceous gland 24 also excretes sebum (not shown) into follicular canal 14. Hair shaft 12 is formed in a supra bulbar region 26 and grows outwardly through follicular canal 14.

An inner root sheath 28 encloses hair shaft 12 along a substantial portion of follicular canal but becomes shrunken and begins to desquamate adjacent its juncture with keratin layer 20. The desquamated inner root sheath cells are shown at 30 and are carried out of follicular canal 14 by the outward growth of hair shaft 12, sebum secretions of sebaceous gland 24 as well as apocrine secretions from apocrine duct 22.

Clearly, of course, the total structure of follicle 10 is much more complex consisting of numerous other units or cellular components. However, this schematic representation of follicle 10 is included herein to more clearly set forth some of the novel features of this invention. In particular, it is important to note that keratin 20 extends interiorly into follicular canal 14 and thereby defining the upper portion thereof while terminating adjacent the upper end of the inner root sheath 28. The natural exfoliation of cells from keratin layer 20 in this region coupled with the desquamated inner root sheath cells 30 along with increased sebum production by sebaceous gland 24 results in plugging of follicular canal 14.

The epithelial tissue underlying keratin layer 20 is an extension of the surface epidermis 16 and forms the structure surrounding follicular canal 14. This layer becomes thinner as it extends downwardly into dermis 18. Normally, the epithelial tissue continually sheds cells that are then carried to the surface by the flow of sebum. However, in acne, the shed epithelial cells are more distinct and durable, and they tend to stick together more readily to form a coherent horny layer that blocks follicular canal 14.

Acne

Acne vulgaris has its origin in pilosebaceous units in dermis 18. These units, consisting of follicle 10 and the associated sebaceous gland 24, are connected to the skin surface by the duct (the infundibulum or follicular canal 14) through which hair shaft 12 passes. The upper part of follicular canal 14 is lined with keratin layer 20 of epidermis 16 and which is also continuous with the skin surface. Sebum is a mixture of fats and waxes excreted by sebaceous gland 24 and passed to the skin surface through follicular canal 14 where it spreads over the skin surface to retard water loss and maintain hydration of the skin and hair. Because sebaceous glands 24 are most common on the face, back, and chest, acne tends to occur most often in these areas.

The histologic characteristics of acne vulgaris are a widely dilated follicular canal 14, a fine villus hair 12, and a large multiacinar sebaceous gland 24 deep in dermis 18. The clinical manifestations of acne are both open and closed comedones, pustules, papules, nodules, and scars. Although acne is rarely pruritic, it is occasionally painful and often leaves serious emotional as well as physical scars.

Acne is a chronic disease that has historically required years of care. Improvement rarely occurs overnight; as a matter of fact, conventional treatment often makes the patient look worse, at least temporarily, and at times it may be unpleasant and even painful. Furthermore, the disease and its treatment often have disturbing psychological effects on the patient.

The current thinking with regard to acne is that at puberty the production of androgenic hormones increases in both sexes. The sebaceous glands, under the influence of this increased hormonal activity, increase in size and activity, producing larger quantities of sebum. At the same time, keratinization of the wall of follicular canal 14 increases and, coupled with the desquamated inner root sheath cells 30, causes mechanical blockage of the increased sebum flow, resulting in dilation of follicular canal 14 and entrapment of sebum and cellular debris. This lesion is a microcomedo, the initial pathologic lesion.

As the microcomedo develops, it distends follicle 10 so that the cellular lining of the wall is stretched and thinned. At this stage, primary inflammation of the follicle wall may develop, with disruption of the epithelial lining and lymphocyte infiltration into and around the follicular wall. A more severe inflammatory reaction results if the follicular wall ruptures or is ruptured by picking or squeezing the lesion, discharging the contents into the surrounding tissue. The epithelial cells, sebum, and any microorganisms present represent foreign substances capable of eliciting an inflammatory reaction.

Current theories explaining the development of inflammatory acne suggest that the initial inflammation of the follicle wall results from the presence of free fatty acids derived from sebum. In particular, triglycerides in the sebum are split by the presence of bacterial lipolytic enzymes to release the fatty acids. The normal bacterial flora in the sebaceous duct are capable of producing these enzymes. The effectiveness of oral tetracycline and topical antibiotics in emollient bases in treating inflammatory acne is due to their ability to suppress the normal bacterial population of the sebaceous duct, thus reducing free fatty acid concentrations.

However, oral antibiotics are accompanied by a number of undesirable side effects that one would prefer not to have if it were possible. The deciding factor being whether the harm from the side effects can be offset by the reduction in the inflammatory acne. On the other hand, the topical application of emollient-based antibiotics presents two problems: first, the emollient base itself is known to penetrate the skin to a significant degree due to the nature of the keratin layer thus carrying a significant portion of the antibiotic into the dermis where it is not required; second, being in an emollient formulation means that it will not readily penetrate the sebum plug in follicular canal 14.

The conventional teaching is that washing is not a therapeutic measure. It merely removes dirt and sebum that have accumulated since the last exposure to soap and water. Furthermore, washing cannot prevent sebum production, because the source of the oil is deep within follicle 10 inaccessible from the surface, nor will scrubbing and the use of abrasives remove comedones. As a matter of fact, vigorous abrasion may induce comedo formation and often converts closed comedones into inflammatory lesions. An axiom that members of the medical profession have found useful when recommending a cleansing is as follows: if the complementary treatment is harsh, a mild cleansing agent, such as an oatmeal or glycerine soap, is recommended; if the subsequent treatment is mild, a stronger cleansing agent, a non-ionic foam or a sulfur-salicylic acid soap, is used.

Historically, the treatment of acne has been as much an art as it is a science. Systemic antibiotics are eminently useful in preventing new inflammatory acne lesions in controlling the inflammatory process. However, the major disadvantages of the systemic treatment of acne is that all drugs exhibit side effects, most of which are unwanted, but tolerated, given the benefits from the taking of the particular drug. Accordingly, topical therapy is considered to be the cornerstone of acne treatment. The two major topical therapeutic agents are tretinoin and benzoyl peroxide derivations. The choice of agent used for initial therapy depends on the predominant type of skin lesion and the type and condition of the skin, whether oily, pigmented, dry, red, or irritable. In most patients with moderate to severe acne, both agents are used concomitantly. Topical agents should be continued for 6 to 12 months after the acne appears to be quiescent; drug strength and frequency of application may be changed depending on the response.

The surface application of antibiotics would seem to be a logical method for treating acne. A variety of preparations are commercially available: 1% clindimycin, 1.5%, and 2% erythromycin, 0.2% tetracycline in a vehicle containing n-decyl methyl sulfoxide, and 1% meclocycline in a creme base. Clindimycin and erythromycin appear to be more effective. For patients with sensitive skin and those living in cold dry climates, the creme base of meclocycline or erythromycin ointment is often better tolerated than the hydroalcoholic vehicles of the other agents. Topical antibiotics are applied once or twice daily and are indicated primarily for papular and pustular acne. Greater therapeutic effect can often be achieved by concomitant use of tretinoin or benzoyl peroxide. The addition of 1.2% zinc acetate to a 4% erythromycin liquid or gel as also resulted in enhanced therapeutic efficacy.

Another theory that I have postulated regarding acne, eczema, and psoriasis involves the immune system and its ability; or rather, its inability to satisfactorily deal with bacteria, particularly bacteria in the follicular canal. I arrived at this conclusion through my extensive experience in working with patients who are afflicted by these various skin conditions. Particularly relevant is the fact that everyone has extensive bacterial populations over the skin surface while only a limited percentage of people suffer from acne or these other skin diseases. Further, it is well known that not all those persons with acne who are being treated systemically through the oral ingestion of antibiotics are successfully treated. Admitted, one finds a temporary remission of some of the acne but upon cessation of the systemic treatment the acne again flares to its prior condition or worse. Two reasons exist for this failure to successfully treat all acne conditions through oral antibiotics: first, the surface of the skin is poorly vascularized so that an insufficient dosage of antibiotic reaches the epidermis and outer portion of the dermis to effectively suppress the causative bacteria; and second, the immune response to the bacteria exacerbates the condition so that even a few residual bacteria are sufficient to create a serious problem. This latter observation further supports my contention that if simple plugging of the follicular canal through increased sebum production as a consequence of increased androgenic hormone production were sufficient to cause acne then everyone should suffer from acne during this phase. Clearly, not everyone develops an acne condition thereby strengthening my contention that acne is primarily a function of the immune response rather than a simple plugging of the follicular canal followed by bacterial proliferation.

With regard to the theory that excessively oily skin, ie., excessive sebum production, as a result of increased hormonal activity is one of the major causes of acne, it must be pointed out that many cases of severe acne are experienced by people having excessively dry skin. The dry skin is a function of inadequate sebum production and yet these people have acne which further supports my theory that acne is primarily an immune response to bacterial activity with a consequent plugging of the follicular canal outlet versus excessive sebum production. Clearly, of course, both conditions will severely exacerbate the acne condition.

Surprisingly, I have discovered that by using my novel discovery, I can successfully treat all acne patients even those who have previously been unsuccessfully treated systemically with antibiotics. Indeed, the success of my invention in treating eczema and psoriasis conditions further implicates the role of the immune system in its response to bacteria involvement in these skin conditions.

It was for the foregoing reasons that I have concluded that it is the immune system's response to certain bacteria on the skin and in the follicular canal in particular that is in reality the causative agent; or, if not the primary causative agent, at least an exacerbative agent in these skin conditions. Thus, in the case of acne, the normal bacterial flora of the hair follicle elicits an immune response that, in turn, reduces the flow capacity of the follicular canal thereby trapping sebum, etc., resulting in comedomegenesis as described hereinbefore.

Regardless of which theory is advanced as the causative agent for acne, my experience has clearly demonstrated the surprising and unexpected results obtained where an aqueous solution of a water soluble antibiotic is applied topically. Importantly, the aqueous solution is formed from the alkaline fraction of an electrolyzed water which presents the antibiotic in its most bioavailable form in the absence of any type of creme, emollient, or the like, which could interfere with its absorption into the keratin layer. Water and particularly the alkaline water, has the added advantage that it is readily absorbed by the keratin layer so that the antibiotic is also intimately dispersed into and held by the keratin layer where it can readily attack and suppress any bacteria with which it comes in contact. This means that the aqueous solution of antibiotic is able to, in effect, assist the immune system by eliminating the bacterial causative agent responsible for the immune response portion of these skin diseases. I also believe that the presence of the alkaline fraction of the electrolyzed water exerts an almost "detergent-like" effect in cutting through any residual oils in either the keratin layer or, more importantly, any residual sebum, etc., in the follicular canal 14 which would otherwise interfere with the antibiotic being carried downwardly therein.

With particular regard to eczema, I have found that once the eczema has been cleared by following the treatment protocol of this invention, the continued use of the maintenance program of this invention for a period of an additional two to three months generally results in a complete cure of the eczema. This discovery further supports my theory that bacteria and the immune response to the bacterial byproducts is one of the leading causes of eczema so that if I can suppress the bacteria I can thereby enable the immune system to, in effect, cure the eczema.

From the foregoing, it is clear that I have both set forth the conventional understanding of these skin conditions as well as my novel theory and novel treatment based on this novel theory. Regardless of which theory is correct, my unique treatment protocol works! Most importantly, it works where others either fail or are only marginally successful.

In light of the foregoing, my discovery that an aqueous solution of a water soluble antibiotic can be used to effectively treat acne, even inflammatory acne, is a truly significant advancement in the art. Even more significantly, I have found that by using the alkaline fraction of an electrolyzed water as the aqueous medium for the water soluble antibiotic substantially improves the ability of the antibiotic to suppress bacteria. Additionally, due to the high affinity of keratin layer 20 for water, the aqueous solution is readily carried down into follicular canal 14 by keratin layer 20. Cleansing of the skin removes most of the waterproofing oils, etc., on the skin so that the application of the aqueous antibiotic solution causes keratin layer 20 to readily "wick" antibiotic solution down into follicular canal 14. I also believe that the presence of the alkaline fraction of the electrolyzed water exhibits what I refer to as a detergent affect to cut through any residual sebum, oils, or oil-based debris, in follicular canal 14. Further, as an aqueous solution, the antibiotic is not accompanied by any nonaqueous medium which could exacerbate the plugging, etc., of follicular canal 14. Another advantage to the use of an aqueous solution is that there is no absorption of the antibiotic by the dermis, hence into the bloodstream, thus no side effects.

Psoriasis

Psoriasis is a major worldwide skin disease with a relapsing character that affects 1% to 2% of the population of Europe and the United States. The diagnosis is primarily based on a series of clinical clues: (1) well-defined erythematous papules or plaques; (2) silvery adherent scales; (3) nail changes (pitting, discoloration, onycholysis, subungual thickening); (4) bilateral and symmetrical distribution; and (5) typical location (scalp, elbows, knees, lumbosacral area). The histopathologic picture of psoriasis is characterized by: (1) Mucro microabscesses or spongiform pustule; (2) epidermal hyperplasia with regular acanthosis, parakeratosis, and absence of the granular layer; and (3) dilated capillaries at the dermal papillae.

The major pathophysiological event in psoriasis is an accelerated epidermal cellular proliferation. Recent evidence suggests an attractive working hypothesis, taking into consideration three features: (1) psoriatic skin contains a greater amount of proteinase; (2) psoriatic epidermis has increased levels of free arachidonic acid and its metabolites, 12-HETE and prostaglandins; and 3) there is epidermal accumulation of polymorphonuclear leukocytes. Thus, arachidonic acid may be released following skin injury and transformed into prostaglandins, 12-HETE, and leukotriene $B_4$. Prostaglandins appear to promote epidermal cell proliferation. Polymorphonuclear leukocytes may be attracted by 12-HETE and leukotriene $B_4$, or by proteinase released after skin injury and through activation of the fifth component of complement. The hydrolase of polymorphonuclear leukocytes may accelerate the rate of epidermal cell division.

In addition, information pointing to a possible connection of psoriasis to immunological mechanisms is also accumulating. The number and function of circulating T lymphocytes, particularly the suppressor T lymphocytes, are decreased. The motility of polymorphonuclear leukocytes and chemotaxis may be altered. Antibodies to stratum corneum and the nuclei of basal epidermal cells have been found. The pathogenetic significance of these changes is, however, unclear at the present time. The British Journal of Dermatology states that psoriasis is characterized by a dysfunction of the skin immunologic system. Which means, of course, that the affected skin is susceptible to secondary bacterial components.

Eczema

Eczema may be defined as an inflammatory disorder of the skin, involving especially the epidermis, which at some stage shows intraepidermal edema (spongiosis). The term dermatitis is used almost synonymously, with subtle nuances varying from person to person. Only in the lay mind does it automatically conjure up visions of some external, usually occupational, and often compensable origin.

The causes of eczema are numerous, and often "constitutional" or idiopathic which is why eczema is referred to by many medical professionals as an atopic dermatitis. In any one patient there are often several causative factors operating together or in sequence. The clinical classification of eczema is unsatisfactory, because it is based partly on etiology and partly on description. Because there are multiple causes, it is not surprising that there is a good deal of overlap between the various named types, and many cases are unclassifiable. Once an eczema has been initiated, many other factors not in themselves able to start an eczema can help to perpetuate it. The eczema thus has some momentum. An ability to break into such a vicious circle is an important part of management.

Diet plays little or no part in the management of most eczemas, but it can be important in atopic dermatitis. Food allergy plays a significant contributory role in some 20% of cases of atopic dermatitis. Even so, 90% of patients are best managed by simple topical therapy. Two to three weeks' avoidance of suspected foods (especially cows' milk in young children) will detect some cases of food allergy. For patients who are more severely affected, who may have multiple allergies, more vigorous elimination diets with careful re-exposure may be indicated, and require the help of an experienced dietitian. Even when a food allergy has been proven, it may no longer be relevant once the eczema has come under control.

Antibacterial Agents are often overused or continued after they are no longer needed, thus risking problems of resistant organisms, sensitization of the skin, and discoloration of skin and clothing. None is ideal, but tetracyclines, neomycin, fusidic acid, quinolines, and mapirocin are all widely used. Often for an infected eczema, a topical steroid is combined with a topical or systemic antibacterial agent. There are many proprietary steroid-antibiotic preparations, each with its own indications and shortcomings.

Medical studies have shown the importance of patient involvement in the treatment process. A number of theories have been advanced to support this concept. The dominant theory appears to be that the patient's attitude toward "wellness" is improved along with a closer compliance with the specific treatment protocol. In the matter of the present invention, I believe that involvement of the patient in not only preparing the aqueous antibiotic solution but also in the meticulous cleansing procedures instills within the patient an awareness about the patient's interaction with his or her external environment. This is important in as far as reducing the incidences of recontamination. Accordingly, not only are the specific steps of this treatment protocol important in and of themselves, but they also teach and train the patient in the steps for better healthcare and/or habits of cleanliness. Our therapy almost always results in a "cure" of a broad range of eczema conditions; i.e., they no longer need the antibiotic to stay clear.

Detailed Description

Antibiotics of the tetracycline family have been prescribed orally for the treatment of acne infections even though the skin surface receives the lowest concentration of the oral antibiotic of any other area or portion of the body. The keratin layer of the epidermis is essentially dead tissue and, therefore, receives no circulation with a corresponding result that it also receives no antibiotic through the circulatory system. Further, the lower layers of the skin receive often less antibiotic than the minimum inhibitory concentration of the antibiotic to be effective. The cornification (clogging of the follicular canal) occurs away from the gland and in the area of the duct which resides mostly in the epidermis which has little circulation present. The infecting agent, *p. acnes,* lives on the surface of the skin so that it infects from the outside in, not inside out.

Importantly, the carrier vehicle of plain, pure water has been selected to keep the application of the antibiotic on the surface of the skin thereby avoiding any active transport of the antibiotic into the lower layers of the skin. Clearly, of course, a minuscule quantity of antibiotic may penetrate into the skin although this is neither desired nor intended since the goal of this invention is to suppress the bacteria on the surface of the skin in keratin layer 20 and in follicular canal 14. The water is changed to slightly alkaline by the electrolysis process.

I have also found that certain water soluble antibiotics or their salts have a relatively short shelf life as an aqueous solution. For example, in aqueous solution chlorotetrocycline hydrochloride loses half its activity in only 24 hours. The aqueous solutions of other antibiotics also become turbid over time due to hydrolysis. Accordingly, it is important that the aqueous solution must be relatively fresh not only for aesthetic purposes but also for the potency of the antibiotic.

In addition to the water therein being readily absorbed by the keratin layer, the antibiotic has no competing factors for binding or loss of effectiveness when dissolved in water. The water is also sterile to preclude recontamination with other, water-born bacterial material. Further, the antibiotic is also lipoid soluble which causes it to bond with the sebaceous secretions in the follicular canal and thereby concentrate itself at the site of the potential infection or in an already infected area. Accordingly, the water is a perfect vehicle in combination of the high water affinity of the keratin for the thorough distribution of the antibiotic without transporting it deeper into the layers of the skin. The water carrier also migrates along the keratin lining of the follicular canal to carry the antibiotic directly to the infection site. The subsequent application of a sterile lotion, skin creme, etc., improves the protection of the skin surface from external bacterial contamination and promotes the preservation of the antibiotic on the skin surface.

The novel skin treatment of this invention involves the following basic steps:

Step One—Preparation of an Aqueous Antibiotic Solution

A water-soluble antibiotic, preferably a doxycycline-type antibiotic is dissolved fresh in a volume of water obtained from the alkaline fraction from an electrolyzed water. The fresh solution is preferred to assure its alkalinity and since certain residual products in the antibiotic can cause the antibiotic to degrade significantly over a period of time when the antibiotic is dissolved in water. The use of a fresh solution of antibiotic and water also avoids the necessity of using any kind of preservative or stabilizing agent which could interfere with or otherwise compromise the integrity or potency of the antibiotic as has been found to be the case with creme-based antibiotic products.

Step Two—Cleansing the Hands

The second step of this novel invention is for the person, usually the patient, to thoroughly cleanse the hands, particularly the fingers which are to be used in the application of the aqueous antibiotic solution. The preferred method is to use warm water and liquid soap dispensed from a pump-type soap dispenser. The pump-type dispenser is preferred since it delivers a quantity of clean soap in contrast to a solid bar of soap that is used by many and offers no assurance that it is not contaminated bacterially.

Step Three—Cleansing the Treatment Area

Using essentially the same protocol for washing the hands, the treatment area is cleansed using a liquid soap pumped from the dispenser. Care is taken at all times to assure that the treatment area is not contacted with any object or solution that could serve as a vector for recontaminating the treatment area with bacteria.

Step Four—Rinsing with Water

The cleansing solution is rinsed with warm (not hot) water and then dried with a clean paper towel or left to air dry. The clean paper towel is used to preclude contaminating the treatment area from a cloth hand towel that may have been handled and/or used by another person previously.

Interim Step Four for Acne Application of Alcohol

For the treatment of acne, a suitable alcohol such as isopropyl alcohol is applied to the acne treatment area. The alcohol performs two functions in the treatment of acne: first, it removes excess oils that were not removed by the cleansing step and, second, it is an effective antibacterial agent against both aerobic and anaerobic bacteria.

Step Five—Application of the Aqueous Antibiotic Solution

The aqueous solution of antibiotic is applied to the treatment area and allowed to air dry. Air drying is a key element of the treatment process because it is believed that the keratin of the epidermal layer absorbs vast quantities of water which, upon evaporation, leaves the antibiotic intimately dispersed throughout the keratin on the outermost layer of the skin. Further, since keratin forms the lining of the upper portion of the follicular canal, the keratin also readily draws the aqueous solution down into the region of the follicle. The antibiotic is thus readily able to destroy any bacteria with which it will come in contact on the skin and in the follicle. Further, certain bacteria can only survive in an aqueous-based environment so that the aqueous solution of antibiotic is in a form that makes it readily available and thus able to attack any bacteria present.

Doxycycline hyclate, in addition to being readily soluble in water, also has a high degree of lipoid solubility so that it is able to attack *p. acnes* in the area of the sebaceous glands. However, it is the dispersal into the keratin particularly the keratin lining of the upper portion of the follicular canal by the alkaline fraction of the water vehicle that places the antibiotic in the position where it can take advantage of its lipoid solubility.

One of the most critical features of this invention other than preventing recontamination of the skin is the use of a freshly prepared solution of a water-soluble antibiotic. Clinical investigations have found that one of the best antibiotics that meets this requirement are the water soluble forms of CECLOR or doxycycline which are water soluble in the hydrate salt (doxycycline hyclate) with no pH sensitivity or breakdown into the inactive ingredients. It is also long acting, has a lower dosage requirement, and is slower to break down in addition to being more biologically active.

All other members of the tetracycline family of antibiotics are either poorly soluble in water or, if compounded as a salt that is readily soluble in water, deteriorate rapidly into an inactive form. Other antibiotics such as erythromycin, clindimycin, and the like are classified as medium spectrum antibiotics and do not appear to possess the desired spectrum of action found in the tetracyclines.

Step Six—Application of a Protective Creme

Although the cleansing steps and the application of an aqueous antibiotic solution are the most important steps in this treatment methodology, it is also important to soothe the skin and thereby reduce the inclination for the patient to want to scratch and thereby reinfect the treatment area. This is done by the application of a suitable creme or lotion to which steroids may or may not be added. In selected instances a physiologically acceptable steroid can be combined with the creme for use on treatment areas where it could be deemed to be beneficial. The topical application of steroids is well known in the art, but not in combination with the novel teachings of this invention.

The application of a suitable creme also tends to "seal" the antibiotic in the keratin layer thereby helping to hold it in intimate contact with the skin. The creme is selected from suitable ingredients so that it does not irritate the already sensitive skin of the treatment area.

Step Seven—Isolating the Treatment Area from Recontamination

The patient is carefully counselled on the importance of maintaining the treatment area free from recontamination. This is done by having the patient provide clean bed linen on a daily basis, bathe and change underclothing on a regular/daily basis, use paper disposable towels where practicable, keep the hands away from the treatment area, alter posture habits where the treatment area is in contact with a chair back, say, as a result of poor posture, etc.

Steps two through six are repeated twice a day or as otherwise directed by the physician. The aqueous antibiotic solution is prepared as needed although it is desirable to limit the total quantity of solution prepared at any one time in order to assure that it is in a relative fresh condition at all times.

Once the patient is cleared of his symptoms and his infection, the above activities are not so important and the patient is allowed to live a more normal life.

EXAMPLE I

A first group of patients was selected for this first study and included 23 subjects of which five voluntarily dropped out of the study in the first month. Even though he had discontinued treatment, one man among these five experienced at least a 90% reduction in his acne condition prior to dropping out of the study, which may partially explain why he dropped out. The remaining eighteen subjects completed the eight to twelve week treatment program. Sixteen of these subjects were classified as successes by the medical professional conducting the study, meaning that the acne condition of each subject was eradicated. Thereafter, a maintenance program was initiated to prevent the acne condition from returning.

The remaining two patients were classified as qualified successes. One of these patients did not keep appointments and, as could best be determined, was not following the instructions. The other patient experienced substantial relief from her acne condition but was unable to obtain complete relief even through she appeared to follow the instructions thoroughly.

EXAMPLE II

A second study group of fifteen subjects was identified and instructed in the steps to follow. All but two subjects were treated successfully. The remaining two subjects were determined not to have an acne condition, one of which had only lipids, white fatty deposits having the appearance of whiteheads.

EXAMPLE III

Ten subjects were identified and treated over an eight to ten week period using the treatment protocol. Of the ten subjects two were cystics and two were borderline cystics.

During the testing period it was discovered that one of the subjects with cystic acne was inadvertently washing the antibiotic off the treatment area shortly after its application. The result of this inadvertence was that after six weeks of treatment this patient experienced almost no improvement. It was further discovered that this subject was not applying the antibiotic solution in the evening. Once these errors were corrected, the subject commenced the treatment program in full and obtained a substantially clear complexion after ten weeks.

The success rate for the remaining subjects was 100%. That is, the complexion of each cleared within eight weeks leaving the skin in a healthy condition. Some residual scarring was present on the subjects with cystic acne.

Importantly, no harmful side effects were observed with any of the subjects. The medical professional conducting this test found the treatment to produce unexpected, surprising, and remarkable results in reducing acne and providing a healthy, clear skin on the treatment areas.

The following are the case histories of these ten patients:

Case History One T. R. was a 23 year old female with moderate acne vulgaris. There were many non-inflammatory closed comedones involving the forehead, chin and malar regions. Also seen were multiple inflammatory pustules, the majority in the malar region and chin but also scattered on the forehead. Diffuse erythema was present in the malar regions. At 8 weeks there were no erythema, pustules or comedones seen.

Case History Two L. T. was a 16 year old female with mild acne vulgarism There were scattered open and closed comedones, inflammatory areola and pustules in greatest number in the malar regions. At 8 weeks there were no inflammatory lesions with rare closed comedones.

Case History Three A. A. was a 15 year old female with moderate to severe acne vulgaris. There were closed and open comedones throughout the entire facial regions with erythema, inflammatory pustules, nodules and cysts in the malar regions. Nodules were tender but nonfluctuant. At 8 weeks there were no inflammatory lesions, except 3 small areola under the left angle of the jaw. Closed comedones were few. There was scarring present in the malar areas.

Case History Four D. C. was a 15 year old female with moderately severe acne vulgaris. There were multiple inflammatory pustules and diffuse erythema involving the forehead, chin and malar area. Closed comedones were present. At 8 weeks the erythema was gone as were the inflammatory lesions. Scattered closed comedones were present in a small number at the hairline.

Case History Five W. C. was a 16 year old male with mild to moderate acne vulgaris. There were multiple inflammatory areola and pustules, generally in chin and malar region. Diffuse erythema was most notably in malar area. Few nonfluctuant nodules were present. At 8 weeks there were no inflammatory lesions. Erythema was cleared.

Case History Six R. F. was a 16 year old male with mild to moderate acne vulgaris. There was erythema and inflammatory areola, pustules and nodules in the malar region and chin. Scattered pustules and nodules were found in the malar region and chin. Scattered pustules and closed comedones were elsewhere. At 8 weeks there were no inflammatory lesions seen. Erythema and comedones were absent.

Case History Seven R. R. was a 16 year old male with mild acne vulgaris. Lesions were mostly closed comedones particularly of forehead with a few inflammatory pustules of the forehead and malar areas. At 8 weeks the subject had moved. By interim visits to the inventor, the patient had shown improvement at 4 weeks.

Case History Eight J. M. was a 16 year old male with severe cystic acne. There were multiple tender nonfluctuant nodules and cysts in the chin, malar and neck regions. Inflammatory areola and pustules were present over most of the facial, neck and back areas. Open and closed comedones were also present. At 8 weeks, there were no nodules, cysts or pustules. A few scattered areola were present generally in the neck region. Scarring was present in the malar and chin regions.

Case History Nine K. K. was an 18 year old male with severe cystic acne. There were tender, fluctuant nodules and cysts in the malar, chin, and neck areas. Most areas involved inflammatory areola and pustules with diffuse erythema in the malar and chin regions. Comedones were diffuse. At 10 weeks, there was scarring without nodules or cysts present. There were no inflammatory lesions or comedones seen.

Case History Ten M. W. was a 15 year old male with moderate acne vulgaris. There were multiple inflammatory pustules, particularly on chin and left malar region. Scattered inflammatory areola, open and closed comedones were present. At 8 weeks there were few inflammatory nodules without pustules. Few scattered closed comedones remained.

Advantageously, I have discovered that the treatment time for patients as described in the foregoing examples can be significantly decreased by around 60% to 80% by the inclusion of electrolyzed water as the solvent for the water soluble antibiotic. This is a remarkable discovery for which at least two theories may be advanced to explain this unexpected result. First, the alkaline fraction may exhibit certain detergent-like characteristics to enable the antibiotic solution to penetrate residual oils and the like both in keratin layer 20 and follicular canal 14. Second, the alkaline character of the alkaline fraction may also decrease the rate of degradation of the antibiotic thus effectively maintaining its potency for a longer period of time.

The precise role played by the topical application of a water-soluble antibiotic is unclear. However, it is currently believed that the surface of the skin, particularly that of a patient suffering from acne, psoriasis, or eczema, is heavily populated with a wide variety of bacterial forms, both aerobic and anaerobic, in the hair follicles, sebaceous glands, etc. Since each of these skin conditions, particularly psoriasis and eczema, cause intense itching with the resultant scratching, I postulate that the skin becomes secondarily infected at the excoriated area by bacteria transported to the affected area by the fingers and fingernails. These bacteria, in turn, find a moist, highly nutritious environment in which to thrive. The metabolic byproducts of the bacteria as well as the presence of the bacteria itself triggers certain of the immune responses which, in turn, causes further swelling, irritation, etc., with an accompanying scratching response, all of which exacerbates an already serious skin condition.

My discovery is that if one can effectively control the presence of bacteria on the affected area of the skin then the natural healing tendency of the skin will take place over a reasonable period of time. I have found that the most effective way to accomplish this control is to first, cleanse the hands and the skin surface; and second, apply an aqueous solution of antibiotic to the skin. Even more advantageously, I have found that a solution of water soluble antibiotic dissolved in the alkaline fraction of an electrolyzed water significantly reduces the overall treatment period. Since the outermost surface of the skin is keratin and keratin has a prodigious capability to absorb water, I believe that the water carries the antibiotic into intimate contact throughout the keratinic surface even into the follicular canal and, upon evaporation of the water, leaves a finely and uniformly dispersed antibiotic across the surface of the skin. The alkaline fraction is believed to not only reduce the degradation of the antibiotic but also to penetrate any residual oils on the skin due to a detergent-like effect of the alkaline fraction. By keeping the skin surface free from recontamination from external sources, the antibiotic is readily able to hold in check if not destroy the bacterial colonies on the skin that are contributing factors for the skin condition in the first place.

Most of the original work that resulted in this discovery was directed toward the treatment of acne. However, one acne patient also had eczema on the fingers of one hand and, since the fingers were subjected to the same treatment protocol as, say, the face, the patient discovered that the eczema condition disappeared. As a result of this fortuitous discovery, the doctor conducting the patient's treatment looked at other skin conditions that could also possibly benefit from my treatment protocol and found that it is also beneficial in the treatment of psoriasis. In all instances, it was found that patients who follow the treatment protocol of my discovery have remarkable results in the alleviation of their skin condition.

Another patient was diagnosed as having eczema on her lower legs. Upon learning of the previous patient's experience, she conducted the treatment protocol on her lower legs and in a matter of a few weeks experienced total recovery from the eczema.

The accounting firm of Ernst & Young performed a medical audit two years after the clinical trials were completed. In the process of reviewing medical records, they also interviewed patients, both acne and eczema, and all remained free of symptoms and were no longer using the active ingredient, i.e, doxycycline.

In conclusion, I have made the surprising discovery that the topical application of an aqueous solution of an antibiotic is highly efficacious in the treatment of certain skin conditions such as acne, eczema, psoriasis, and the like. Importantly, the topical application of an aqueous solution of an antibiotic is superior to the topical application of emollient or creme-based antibiotics for the reasons that: (1) the antibiotic is freshly prepared and thus is characterized by the absence of preservatives, or the like, and is also presented in its most bioavailable form; (2) the aqueous solution of antibiotic will not penetrate into the skin as will emollient or creme-based antibiotic applications; (3) the water is quickly and thoroughly absorbed into the keratin layer whereas emollients and cremes are not; (4) using this phenomena, the keratin lining of the upper end of the follicular canal draws the aqueous solution of antibiotic down into the follicle where it can readily attack the bacteria present; (5) the water does not shield any bacteria, particularly anaerobic bacteria, from attack by oxygen; (6) the aqueous solution must be freshly prepared in order to assure its freshness and the absence of degradation products, preservatives, and the like. Even more importantly, the use of the alkaline fraction of an electrolyzed water both extends the potency of the antibiotic and helps cut through any residual oils due to its detergent-like effect thereby rendering the antibiotic significantly more effective.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for topically dispersing a water-soluble antibiotic throughout the keratin layer of a preselected area of the skin comprising the steps of:

cleansing said area of the skin;

electrolyzing water to produce an alkaline fraction of said water;

preparing an aqueous solution of said water-soluble antibiotic by dissolving a physiologically acceptable amount of said water-soluble antibiotic in said alkaline fraction of said water;

applying said aqueous solution of said water-soluble antibiotic to said area of the skin;

wicking said aqueous solution of said water-soluble antibiotic into said keratin layer, said keratin layer absorbing said water from said aqueous solution of said water-soluble antibiotic, said water thereby carrying said antibiotic into intimate dispersal throughout said keratin layer; and evaporating said water from said keratin layer thereby leaving said water-soluble antibiotic in intimate dispersal throughout said keratin layer.

2. The method defined in claim 1 wherein said cleansing step is preceded by cleaning the hands prior to cleansing said area of the skin to reduce contamination from said area of the skin by said hands.

3. The method defined in claim 1 wherein said cleansing step includes applying an alcohol to said area of the skin prior to said dispersing step when said area of the skin is characterized by the presence of an acne condition.

4. The method defined in claim 1 wherein said wicking step includes penetrating any residual oils in said keratin layer with a detergent-like action of said alkaline fraction.

5. The method defined in claim 1 wherein said evaporating step includes applying an emollient creme to said area of the skin to seal said antibiotic in said keratin.

6. The method defined in claim 5 wherein said applying step includes selecting said emollient creme from a creme containing a steroid.

7. The method defined in claim 1 wherein said evaporating step includes preventing contaminated objects from contacting said area of the skin.

8. The method defined in claim 1 wherein said preparing step includes extending the potency period of said water-soluble antibiotic by dissolving said water-soluble antibiotic in said alkaline fraction of electrolyzed water.

9. A composition for treating a preselected area of the surface of the skin with a dispersion of an antibiotic throughout a portion of the keratin layer of the epidermal layer of the area of skin comprising:

a water soluble antibiotic;

an alkaline fraction of an electrolyzed water.

a physiologically acceptable quantity of said water soluble antibiotic dissolved in said alkaline fraction of said electrolyzed water to form an aqueous solution of said water soluble antibiotic; and wick means for dispersing said water soluble antibiotic intimately throughout said keratin layer of said preselected area, said alkaline fraction of said electrolyzed water being absorbed by said keratin layer, said absorbed water carrying said antibiotic into said keratin layer with said water upon subsequent evaporation leaving behind said antibiotic dispersed throughout said keratin layer.

10. The composition defined in claim 9 further including cleansed hands and cleansed preselected area to improve absorption of said alkaline fraction of electrolyzed water and to minimize contamination of said preselected area.

11. The composition defined in claim 9 wherein said cleansed preselected area includes an alcohol applied to said preselected area when said preselected area is characterized by the presence of acne.

12. The composition defined in claim 9 comprising an absence of recontamination of said preselected area by isolation of said preselected area.

13. The composition defined in claim 9 wherein said alkaline fraction of electrolyzed water comprises an extender for extending the potency of the water soluble antibiotic.

14. The composition defined in claim 9 wherein said alkaline fraction of electrolyzed water comprises a detergent for cutting residual oils.

15. A method for treating a skin condition selected from the group consisting of acne, eczema, and psoriasis comprising:

obtaining a water soluble antibiotic;

preparing an alkaline fraction of water from an electrolyzed water;

dissolving a physiologically effective amount of said water soluble antibiotic in said alkaline fraction of water to form an aqueous solution of said water soluble antibiotic;

cleaning the hands;

cleansing the area of said skin condition;

applying said aqueous solution to the keratin layer of said area by using the cleaned hands;

absorbing said alkaline fraction of water from said aqueous solution with the keratin layer of said skin condition thereby intimately dispersing said antibiotic over said skin condition;

evaporating said alkaline fraction of water from said aqueous solution leaving a residue of said water soluble antibiotic dispersed in said keratin layer; and sealing said antibiotic in said keratin layer by applying a creme to said skin area.

16. The method defined in claim 15 wherein said cleansing step includes applying an alcohol to said area when said area is characterized by the presence of an acne condition.

17. The method defined in claim 16 wherein said applying step comprises directing said aqueous solution downwardly into the follicular canals of the skin affected by said skin condition by absorbing said aqueous solution with the keratin layer of the follicular canals.

18. The method defined in claim 17 wherein said directing step includes cutting residual oils in the follicular canals with said alkaline fraction of water.

19. The method defined in claim 15 wherein sealing step is followed by an isolating step wherein said skin area is isolated from contacting infective surfaces to preclude reinfection of said skin area with bacteria.

20. The method defined in claim 15 wherein said dissolving step includes extending the potency of said water soluble antibiotic by dissolving said water soluble antibiotic in said alkaline fraction of water.

* * * * *